United States Patent [19]

Baldwin

[11] 4,425,372
[45] Jan. 10, 1984

[54] PROCESS FOR MAKING ABSORBENT BIOACTIVE WETTABLE MEDICAL FABRIC

[75] Inventor: A. Frank Baldwin, Greensboro, N.C.

[73] Assignee: Burlington Industries, Inc., Greensboro, N.C.

[21] Appl. No.: 400,223

[22] Filed: Jul. 20, 1982

Related U.S. Application Data

[63] Continuation-in-part of Ser. No. 310,414, Oct. 9, 1981.

[51] Int. Cl.³ .............................................. A01N 1/02
[52] U.S. Cl. ...................................... 427/2; 427/389;
427/389.9; 427/391; 427/392; 427/393.1;
427/393.3
[58] Field of Search ............... 427/2, 243, 244, 389.9,
427/393.1, 393.3, 392, 391, 389; 252/8.8, 8.9;
8/490; 128/132 D

[56] References Cited

U.S. PATENT DOCUMENTS

| | | | |
|---|---|---|---|
| 3,730,701 | 5/1973 | Isquith et al. | 71/67 |
| 4,005,030 | 1/1977 | Heckert et al. | 252/140 |
| 4,005,117 | 1/1977 | Heckert et al. | 252/548 |
| 4,006,176 | 2/1977 | Heckert et al. | 252/541 |
| 4,184,004 | 1/1980 | Pines et al. | 427/387 |
| 4,283,519 | 8/1981 | Pines et al. | 427/387 |

FOREIGN PATENT DOCUMENTS 1175120 12/1969 United Kingdom.
1367666 9/1974 United Kingdom.

*Primary Examiner*—Thurman K. Page
*Attorney, Agent, or Firm*—Cushman, Darby & Cushman

[57] ABSTRACT

An absorbent, highly wettable, bioactive fabric useful as a surgical drape, dressing or the like comprised of a non-cellulosic substrate having a non-leachable silicone quaternary bioactive compound together with a hydrophilic organosilicone terpolymer incorporated thereon is described. The fabric is used to isolate a surgical incision site and provides an absorbent antimicrobial field to destroy migrating and cross-contaminating bacteria, fungi and algae. Procedures for producing the fabric are also disclosed.

13 Claims, 1 Drawing Figure

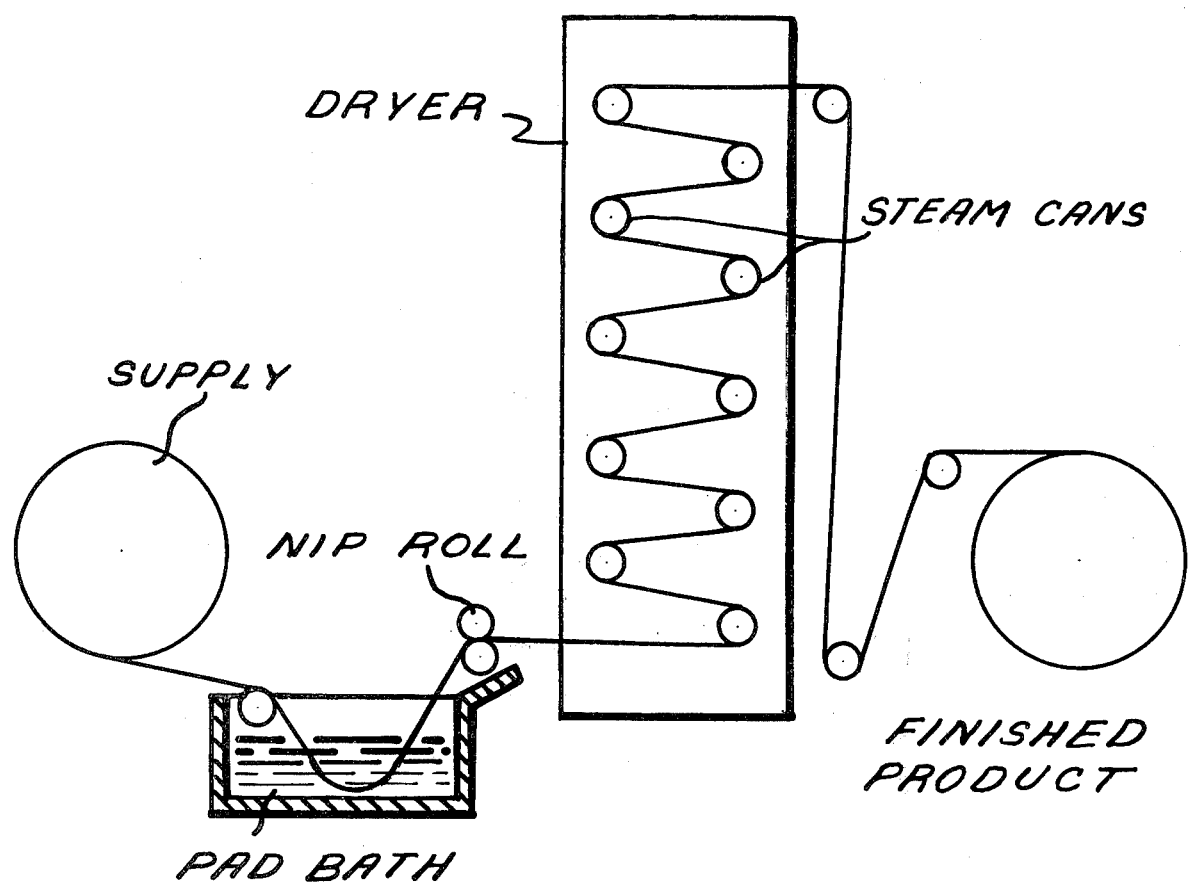

ions occurs it must be virtually undetectable, i.e. only less than 0.2 parts per million (0.2 ppm) from a 1.2 inch × 1.2 inch swatch according to test procedures, described in more detail below. Non-leachability or substantial non-leachability is a factor of the fabric sample or swatch size being tested.

PROCESS FOR MAKING ABSORBENT BIOACTIVE WETTABLE MEDICAL FABRIC

CROSS-REFERENCE TO RELATED APPLICATIONS

This application is a continuation-in-part of my earlier application Ser. No. 310,414 filed Oct. 9, 1981.

This invention relates to an absorbent fabric suitable for use as a surgical drape, dressing or the like which is used to isolate a surgical incision site and at the same time provides an absorbent antimicrobial field which becomes substantive on the fabric and services to destroy migratinng and cross-contaminating bacteria, fungi and algae. Procedures for producing this fabric are also disclosed. Such fabric is highly wettable, bioactive and serves to lower the amount of microbial contamination while lowering the risk of post-operative infection.

BACKGROUND OF THE INVENTION

A need exists for a surgical drape, bandage or like product that kills bacteria but is itself non-toxic, that provides permanent antimicrobial capacity yet the antimicrobial agent itself is not extracted from the fabric in use and that maintains its effectiveness over a period of time but is not inhibited by sterilization, storage or handling.

A particularly useful antimicrobial agent is Q9-5700, an antimicrobial agent available from Dow Corning Corporation of Midland, Michigan. The material is a silicone quaternary amine, chemically 3-(trimethoxysilyl)-propyloctadecyl dimethyl ammonium chloride. This material has been used to protect textiles and inhibit odor-causing bacteria and fungi which contamination may result in odor problems, discoloration and deterioration of these textiles. Application of this type of silicone quaternary amine onto the surface of textiles has been found to inhibit the growth of microorganisms and to aid in the control of the above-mentioned problems. As such it is authorized by the Environmental Protection Agency of the U.S. Government for use on textile surfaces (EPA No. 34292-1) and it has also been accepted by the Food and Drug Administration of the U.S. Government for use in medical devices for use in association with humans and animals.

Surgical drapes and like materials are typically made of non-woven textiles or other non-woven type materials, however when such silicone quaternary amines are applied to a non-woven substrate it was found that the substrate was rendered hydrophobic, thus aqueous-based fluids, including normal body fluids, were repelled by such a coated substrate. Further difficulties were encountered in maintaining the integrity of the silicone quaternary amine in or on the substrate and preventing it from leaching away from the substrate and possibly contaminating patient's surface area surrounding the site of the surgical procedure and even possibly contaminating the surgical opening itself.

The requirements for a successful medical fabric or substrate include the following:

1. The substrate must be bioactive, that is it much achieve a 95% or better bactericidal effect within one hour. In other words, the material is bacteriocidal and not merely bacteriostatic as is the case with the wearing apparel.

2. The bioactive/bactericidal material must remain on the substrate and not be leached from the substrate, but if leaching occurs it must be virtually undetectable, i.e. only less than 0.2 parts per million (0.2 ppm) from a 1.2 inch × 1.2 inch swatch according to test procedures, described in more detail below. Non-leachability or substantial non-leachability is a factor of the fabric sample or swatch size being tested.

3. The leachate removed from a sample of the medical substrate must not exhibit cytotoxicity to cells. This includes not only the antimicrobial agent itself but also other finishes, colorants or the like that may also be applied to the substrate. A typical testing procedure includes adding a standardized cell culture to a leachate recovered from a predetermined sample size of the substrate being tested, incubating the culture plus leachate and observing the culture for either cell death or morphological change to the cells in the culture.

4. The medical substrate must be non-flammable in accordance with standard CS-191-53.

5. The medical substrate must conform to the anti-static requirements of test NFPA 56-A.

6. The substrate itself must be absorptive of normal body fluids, such as physiological saline, and blood.

It has been a continuing difficulty in the art to identify an appropriate finishing agent or group of agents that will inhibit the hydrophobicity imparted to the substrate by the silicone quaternary amine antimicrobial agent and provide a substrate conforming to the six requirements identified above. Virtually all detergents commonly used as fabric softeners are leachable from a non-woven substrate and tend to lyse cells to at least some extent. For example, to be successfully used organic non-ionic surfactants may require a substantial amount of the surfactant on the substrate, for instance from 5 to 15%, calculated on the weight of the fabric.

Another difficulty encountered is in the selection of an appropriate substrate is that the silicone quaternary amine-type antimicrobial compounds do not readily adhere to polyester substrates and that as such the resulting product does not conform to the maximum leachability requirements, as stated above. Accordingly cellulsoic substrates are preferred, although minor amounts of polyester in a cellulosic/polyester blend may be tolerated.

BRIEF DESCRIPTION OF THE DRAWING

The attached drawing schematically represents the process of my invention.

DETAILED DESCRIPTION OF THE INVENTION

I have found, and hereby disclose, a process for preparing an absorptive, bacteriostatic non-woven medical substrate in which a solution of a specific silicone quaternary amine is applied conjointly with a member of a specific class of rewetting agents which in the system of the invention act as hydrophilic coupling agents. Such rewetting agents impart the necessary water absorptive qualities in the product yet become substantive (non-leachable) on the fabric meeting the bioactivity, leachability, cytotoxicity, non-flammability, anti-static and absorptive properties enumerated above.

I have found that an aqueous-based solution preferably containing: (1) from about 0.2 to about 1.1% of 3-(trimethoxysilyl)-propyloctadecyl dimethyl ammonium chloride as the microbiocide, together with (2) from about 0.5 to 1.5 weight % of an epoxy-polyoxyalkylene modified organosilicone as a hydrophilic coupling agent, sometimes referred to as a "rewetter" herein, when applied to a suitable non-woven cellulosic-based substrate will produce a waxy, water-insoluble, bioactive, absorbent, wettable finish on the material which retains both the bioactive material and the hydrophilic coupling agent yet conforms to the necessary cytotoxicity, non-flammability and anti-static requirements listed above.

While not wishing to be bound by any particular theory it appears that a combination of the two materials, which may be applied separately but preferably together, produces a type of crosslinked matrix reactively bonded to the fiber of the substrate. The presence of the epoxy-polyoxyalkylene organosilicone material in the treatment bath serves not only to provide the necessary rewetting/absorptive qualities for the finished product but also prevents the silicone quaternary amine bioactive material from complexing and becoming gelled during processing operations thus extending shelf life and reducing the loss of microbiocide from the solution. The aqueous-based solutions used in the process of my invention are typically applied by padding onto a suitablee non-woven substrate although other application procedures may be used.

Over a period of continued use it was observed that a pad bath containing only an aqueous solution of the silicone quaternary amine bioactive material become contaminated with metal ions, such as sodium, calcium, lithium, barium, potassium and magnesium, which ions are frequently contained in the cellulosic substrate as a result of its manufacturing procedure. For instance, over a period of a few hours during continued application I have observed apparent homo-polymerization of the silicone quaternary amine bioactive compound pad bath which homo-polymerization eventually gells the entire pad bath. The bath must be discarded, however as the bioactive material is the subject of U.S. government regulations and must be carefully inventoried; it is also necessary to "neutralize" the material prior to discharging the gelled pad bath. Unexpectedly I have found that the presence of a rewetter/surfactant material in the pad bath prevents the bath from gelling. Nonionic surfactant materials present in amounts of from 0.5 to 3.0 times the solid concentration of the silicone quaternary amine bioactive material may be used. However, due to its superior value as a rewetter I prefer to use the epoxy polyoxyalkylene modified organosilicone material of the type mentioned above and described in more detail below.

Suitable non-woven substrates are used in the process of my invention are essentially all cellulosic in nature and include paper, cotton, rayon and possibly wool, but not the substrates composed essentially entirely of an acrylic, polyester or nylon fiber. The preferred substrate is a dry laid spray bonded paper toweling material which is bonded with acrylic resins and contains about 80–85% by weight paper (cellulose) with 15–20% by weight acrylic resin binder. This material is available from the Fort Howard Paper Company under their style designation E-34. Also suitable is a wet-laid paper that is creped and print bonded and which is composed of about 90% by weight cellulose and about 10% by weight acrylic binder. Such materials include the Scott Hi-Loft materials under style designations 3051 and 3055 available from the Scott Paper Company. Non-woven substrates containing significantly less than about 80% cellulosic content are not preferred.

The procedure of my invention will now be described with reference to the attached drawing. As shown in the figure a non-woven substrate is directed from a supply reel through a pad bath (the content of which are explained below) and passed through a nip roll to achieve an overall wet pickup (wpu) of between about 75 and 125% calculated on the weight of the non-woven substrate. Preferably the wet pickup is in the range of about 85 to about 115% also expressed on the weight of the substrate. Next the impregnated substrate is passed through a stack of steam cans maintained at a suitable temperature so that dry/cure occurs at between about 280° and 360° F. As the wet material is passed over the series of steam cans the lower stack of cans tends to remove the water and dry the material while the upper stack of cans adds additional heat and cures the material setting the applied components to the substrate. Preferably the material is subjected to a temperature in the range of 280°–300° F. for at least about 5 seconds. The dried, finished product is then led away from the stack of steam cans, rolled and stored wrapped in plastic bags or the like.

The preferred silicone quaternary amine bioactive material is 3-(trimethoxysilyl)-propyloctadecyldimethyl ammonium chloride which is described in U.S. Pat. No. 3,730,701, the disclosure of which is hereby incorporated by reference. A class of suitable bioactive silyl quaternary amine compounds have the formula:

$$(CH_3O)_3Si(CH_2)_3\overset{(CH_3)_2}{\underset{R^{1\ominus}}{N^{\oplus}}}-R$$

in which R is a $C_{11-22}$ alkyl group and $R^1$ is chlorine or bromine. The preferred silicone quaternary amine is 3-(trimethoxysilyl)-propyloctadecyl dimethyl ammonium chloride and is available as a 42% active solids in methanol from Dow Corning Corporation of Midland, Michigan under the designation DC-5700 (formerly Q9-5700). This material is well accepted in commerce and has been approved not only as a bacteriostatic textile treatment but also as a bactericidal component for medical device/non-drug applications.

As the hydrophilic coupling agent there is used a member of the class of the epoxy-polyoxyalkylene modified organosilicones described in U.S. Pat. No. 4,184,004, the disclosure of which is incorporated herein by reference. The preferred material is available in commerce from Union Carbide Corporation and is believed to respond to the following general structure:

$$MD_xD'_yD''_zM$$

in which the units are end-capping units and are identical to each other, the various "D" and "M" units having the following configuration:

ENLARGED STRUCTURE

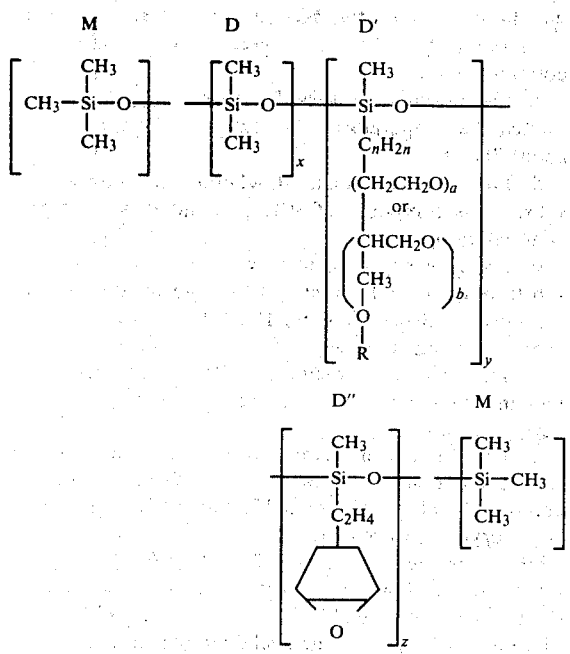

as disclosed in U.S. Pat. No. 4,184,004. In the above formula R represents either hydrogen or methyl and the total of a+b is believed to be from 5 to 200. The average values of x, y and z are as follows:

x = 10 to 50,000;
y = 1 to X;
z = 1 to 0.5x provided that,
y+z ≦ 0.75x preferably:

x = 25 to 1,000;
y = 1 to 0.5x provided that,
z = 1 to 0.25x and
y+z ≦ 0.5x most preferably:

x = 50 to 300
y = 1 to 0.25x
x = 1 to 0.15 x, provided that
y+z ≦ 0.25 x as disclosed at column 3 lines 35-50 of U.S. Pat. No. 4,184,004.

This particular combination of hydrophilic coupling agent and bioactive compound is believed to be substantive on the fabric in accordance with the following scheme:

For purposes of illustration the natural fiber, i.e. cellulose, surface may be depicted as having a series of hydroxyl groups extending therefrom. Thus a possible linking reaction between the bioactive silyl quaternary amine and the cellulose may be:

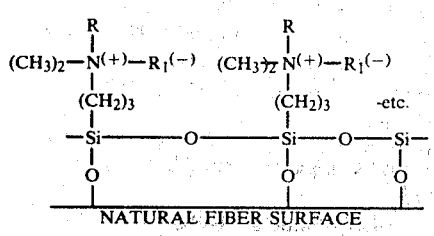

a possible linking reaction between the hydrophilic organosilicone terpolymer may be:

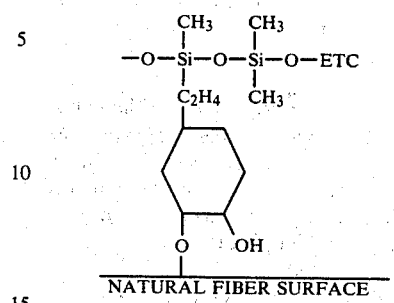

and linking between the quaternary amine and the organosilicone terpolyer may be:

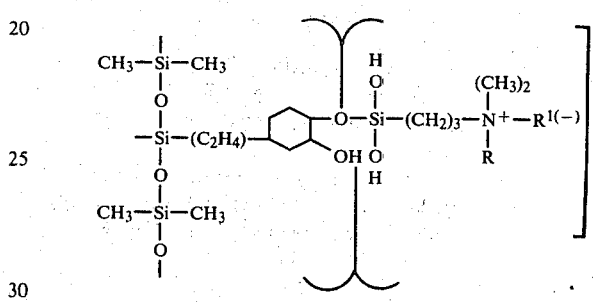

As illustrated, the cyclohexyl epoxy group of the coupling agent combines with the trihydroxy silyl group of the bioactive compound to form a complex which, when contacted with a cellulosic substrate, forms a carbon-oxygen bond, probably a covalent bond, with the substrate by removal of one mole of water.

The manner in which the bioactive compound plus hydrophilic coupling agent are placed onto the substrate may be by brushing, spraying or other suitable means known in the textile arts. I prefer to apply the required components onto the substrate by padding them using a pad bath having generally the following ingredients and amounts:

|  | range | example |
|---|---|---|
| bioactive compound | 0.2-1.1% | 1.0% |
| epoxy-polyoxyalkylene hydrophilic coupling agent | 0.5-1.5% | 1.0% |
| alcohol (solvent) | 1-3% | 1.0% |
| water | balance | balance |

As shown in the above table, the amount of the bioactive compound is prferably within the range of about 0.2 to about 1.1% calculated on the weight of the solids present in the pad bath. An amount substantially greater than 1.1% is difficult to retain on the medical substrate without leachability difficulties. The alcohol is used to solubilize the hydrophilic coupling agent which is then added to the bioactive compound to formulate the pad bath.

The pad bath must be applied to the substrate within reasonable temperature limits, for instance room temperature up to about 35° F. otherwise the bath may become unstable and the pad bath itself will react with the sides of its container. Accordingly it is appropriate to prepare the pad bath using cold water and to protect the bath from extreme temperature conditions during storage and operations.

The medical substrate so produced must exhibit an absorptive capacity generally in accordance with ASTM D1117 and demonstrate a suitable ability to absorb and retain water.

Applications for the materials produced by the herein described process include various medical-type substrates such as non-woven bed covers, liners and sheets, bandages, dressings, instrument wraps, instrument tray liners, hospital gowns, caps and garments, surgical drapes as well as many other applications.

What is claimed is:

1. A process for making an absorbent, bioactive wettable medical fabric comprising the steps of:
    (a) applying to a non-woven cellulosic-containing substrate (1) a bioactive amount of a bioactive silyl quaternary amine compounds have the formula:

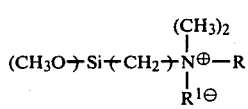

wherein R is an alkyl of 11 to 22 carbon atoms and $R^1$ is a bromine or chlorine; and (2) a wettable hydrophilic coupling amount of an organosilicone terpolymer of the formula:

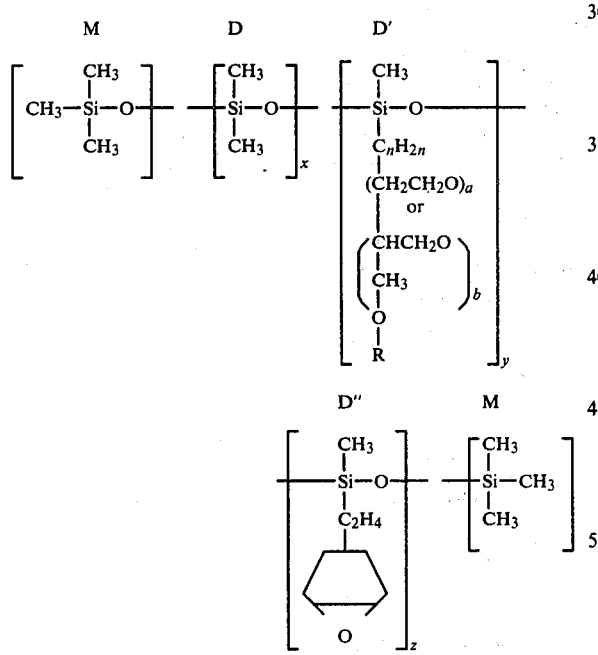

wherein R is hydrogen or methyl, the sum of a+b is in the range of 5 to 200, x is 10 to 50,000, y is 1 to x and z is 1 to 0.05x provided that the sum of y+z is ≦0.75x; and
    (b) heating the thus coated substrate from step (a) to dry the substrate and fix the microbiocide and hydrophilic coupling agent to said substrate, thereby producing bacteriocidal substantially non-leachable and non-flammable finish which is substantive on said substrate.

2. The process of claim 1 wherein the microbiocide and the hydrophilic coupling agent are applied together in the same pad bath.

3. The process of claim 2 wherein said pad bath is an aqueous solution containing from about 0.2 to about 1.1 weight percent of the bioactive agent (1) and from about 0.5 to about 1.5 weight percent of the hydrophilic coupling agent (2).

4. The process of claim 1 wherein step (b) is conducted at a temperature in the range of about 280° F. to about 360° F.

5. The process of claim 1 wherein said non-woven substrate is composed of at least about 80 weight percent cellulose.

6. The process of claim 5 wherein said non-woven substrate contains from about 80 to 85 weight percent cellulose bonded with about 15 to about 20 weight percent acrylic resin binder.

7. The process of claim 3 or 4 wherein said non-woven substrate is composed of at least about 80 weight percent cellulose.

8. The process of claim 7 wherein said non-woven substrate contains from about 80 to 85 weight percent cellulose bonded with about 15 to about 20 weight percent acrylic resin binder.

9. The process of claim 1, 2, 3, 4 or 6 wherein said microbiocide (1) is 3-(trimethoxysilyl)-propyloctadecyl dimethyl ammonium chloride and said hydrophilic coupling agent (2) is an organosilicone terpolymer of the formula:

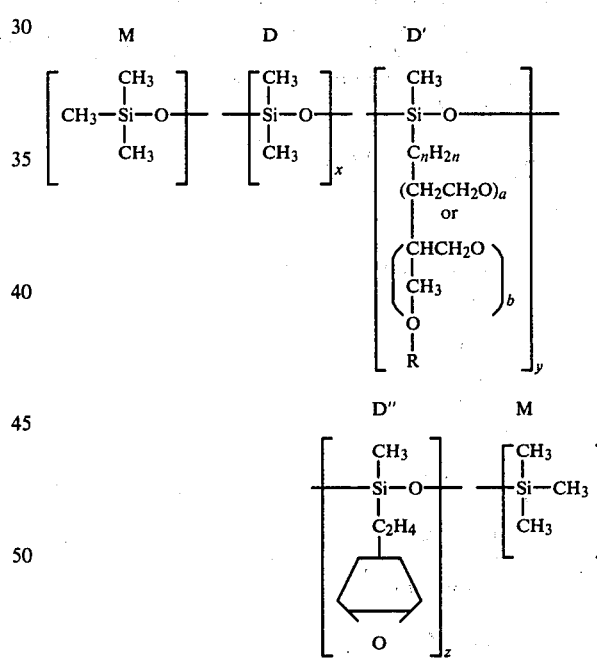

wherein R is hydrogen or methyl, the sum of a+b is in the range of 5 to 200, x is 50 to 300, y is 1 to 0.25x and z is 1 to 0.5x, provided that the sum of y+z is ≦0.25x.

10. A process for making an absorbent, bioactive, wettable medical fabric comprising the steps of:
    (A) applying to a non-woven substrate containing at least about 80% cellulose an aqueous solution containing:
        (i) a bioactive amount of 3-(trimethoxysilyl)-propyloctadecyl dimethyl ammonium chloride, and
        (ii) a hydrophilic coupling amount of an organosilicone terpolymer of the formula:

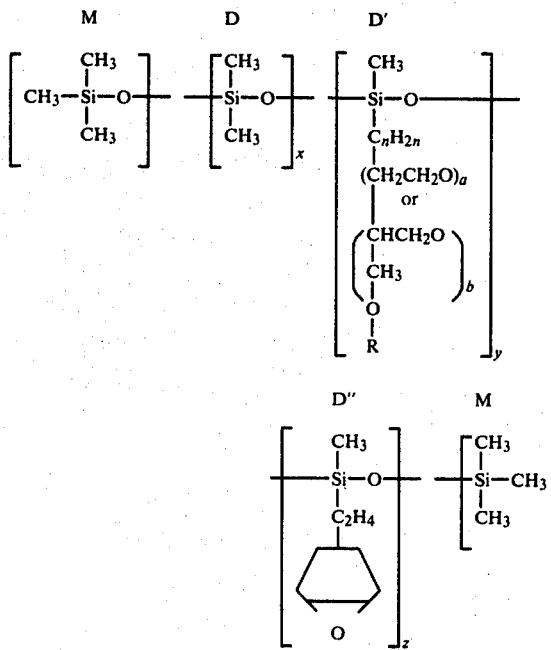

wherein R is hydrogen or methyl, the sum of a+b is in the range of 5 to 200, x is 50 to 300, y is 1 to 0.25x and z is 1 to 0.5x, provided that the sum of y+z is $\leq 0.25x$; and (B) heating the thus applied substrate of step (A) at a temperature in the range of about 280° F. to about 360° F. for a period of time sufficient to dry the applied aqueous solution and to attach the microbiocide (i) and hydrophilic coupling agent (ii) to the cellulose fibers of the substrate such that components (i) and (ii) are substantially non-leachable from the substrate, the resulting fabric being bacteriocidal, substantially non-leachable, non-cytotoxic, substantially completely non-flammable and static resistant and capable of absorbing body fluids.

11. The process of claim 10 wherein the aqueous solution contains from about 0.2 to about 1.1 weight percent of component (i) and about 0.5 to about 1.5 weight percent of component (ii).

12. The process of claim 10 or 11 wherein said substrate contains from about 80 to about 85 weight percent cellulose bonded with about 15 to about 20 weight percent acrylic resin binder.

13. The absorbent, bioactive wettable medical fabric produced by the process of claim 10.

* * * * *

UNITED STATES PATENT AND TRADEMARK OFFICE
Certificate

Patent No. 4,425,372          Patented January 10, 1984

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is A. Frank Baldwin, Greensboro N.C.; Stuart P. Suskind, Valencia, Calif.; Donald M. Patterson, El Paso, Tex.

Signed and Sealed this nineteenth Day of August, 1986.

BRADLEY R. GARRIS,
*Office of the Deputy Assistant Commissioner for Patents.*